US012589120B2

(12) United States Patent (10) Patent No.: US 12,589,120 B2

Karamanian (45) Date of Patent: Mar. 31, 2026

(54) METHODS OF TREATING EPIDERMOLYSIS BULLOSA WITH CELL-FREE AMNIOTIC FLUID COMPOSITIONS

(71) Applicant: Eliksa Therapeutics, Inc., Doylestown, PA (US)

(72) Inventor: Armen A. Karamanian, Newtown, PA (US)

(73) Assignee: Eliksa Therapeutics, Inc., Doylestown, PA (US)

( * ) Notice: Subject to any disclaimer, the term of this patent is extended or adjusted under 35 U.S.C. 154(b) by 569 days.

(21) Appl. No.: 17/964,403

(22) Filed: Oct. 12, 2022

(65) Prior Publication Data

US 2023/0114217 A1 Apr. 13, 2023

Related U.S. Application Data

(60) Provisional application No. 63/274,214, filed on Nov. 1, 2021, provisional application No. 63/254,918, filed on Oct. 12, 2021.

(51) Int. Cl.
| | |
|---|---|
| *A61K 35/50* | (2015.01) |
| *A61K 38/18* | (2006.01) |
| *A61K 38/39* | (2006.01) |
| *A61P 17/00* | (2006.01) |
| *A61P 17/02* | (2006.01) |

(52) U.S. Cl.
CPC ............ *A61K 35/50* (2013.01); *A61K 38/185* (2013.01); *A61K 38/39* (2013.01); *A61P 17/00* (2018.01); *A61P 17/02* (2018.01)

(58) Field of Classification Search
None
See application file for complete search history.

(56) References Cited

U.S. PATENT DOCUMENTS

| | | | |
|---|---|---|---|
| 2018/0104186 A1* | 4/2018 | Badiavas | ............. A61K 9/0014 |
| 2018/0250343 A1* | 9/2018 | Reems | .................... A61L 24/08 |

FOREIGN PATENT DOCUMENTS

| | | |
|---|---|---|
| WO | 2017147587 A1 | 8/2017 |
| WO | 2019060719 A1 | 3/2019 |
| WO | 2020176801 A1 | 9/2020 |

OTHER PUBLICATIONS

Lo et al. (2009) J. Am. Acad. Dermatol. vol. 62, No. 6: 1038-1044. (Year: 2009).*
International Search Report and Written Opinion for corresponding PCT/US2022/077987, mailed Jan. 16, 2023, 13 pages.
Chacón-Solano et al. 2022 Matrix Biol. 111:189-206.
Bruckner-Tuderman et al. 2010 J. Invest.Dermatol. 130:1485-1488.
Fritsch et al. 2008 J. Clin. Invest. 8;118(5):1669-1679.
Nyström et al. 2015 EMBO Mol. Med. 7(9):1211-1228.
Odorisio et al. 2014 Human Mol. Genet. 23:15;3907-3922.

* cited by examiner

*Primary Examiner* — Russell G Fiebig
(74) *Attorney, Agent, or Firm* — WOMBLE BOND DICKINSON (US) LLP; Danielle L. Herritt; Seiko Okada

(57) ABSTRACT

Provided herein are methods of treating a subject having epidermolysis bullosa, comprising administering to the subject a therapeutically effective amount of a pharmaceutical composition comprising amniotic fluid substantially free of endogenous cells.

20 Claims, 3 Drawing Sheets

EB-Fibroblasts

EB-Fibroblasts + acAF

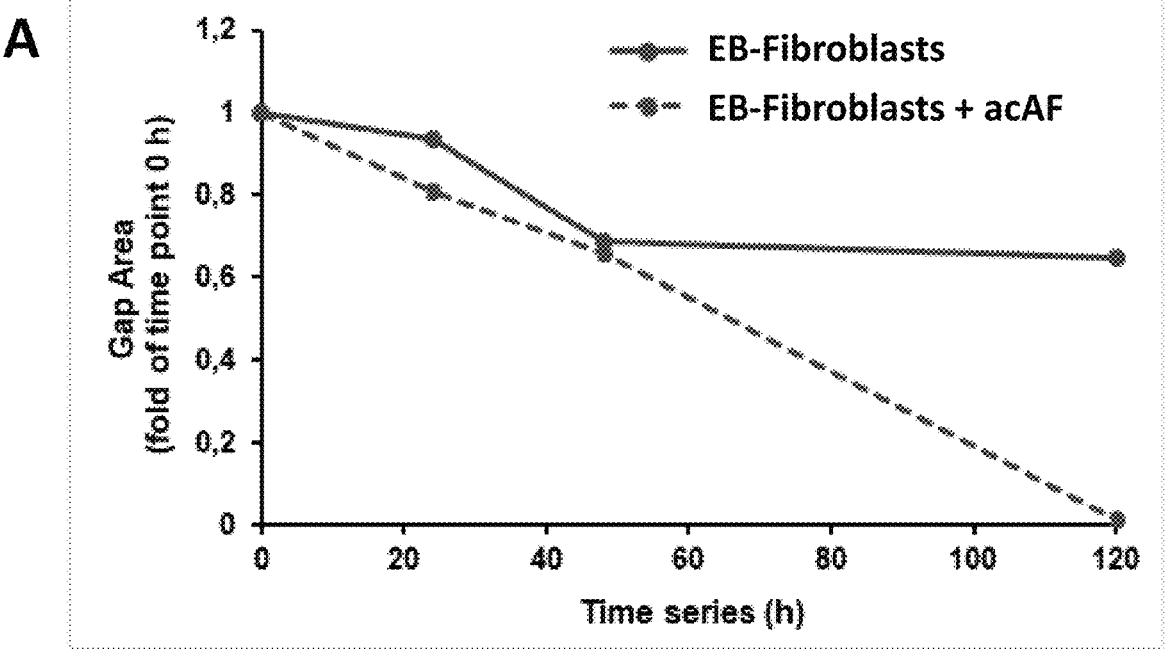
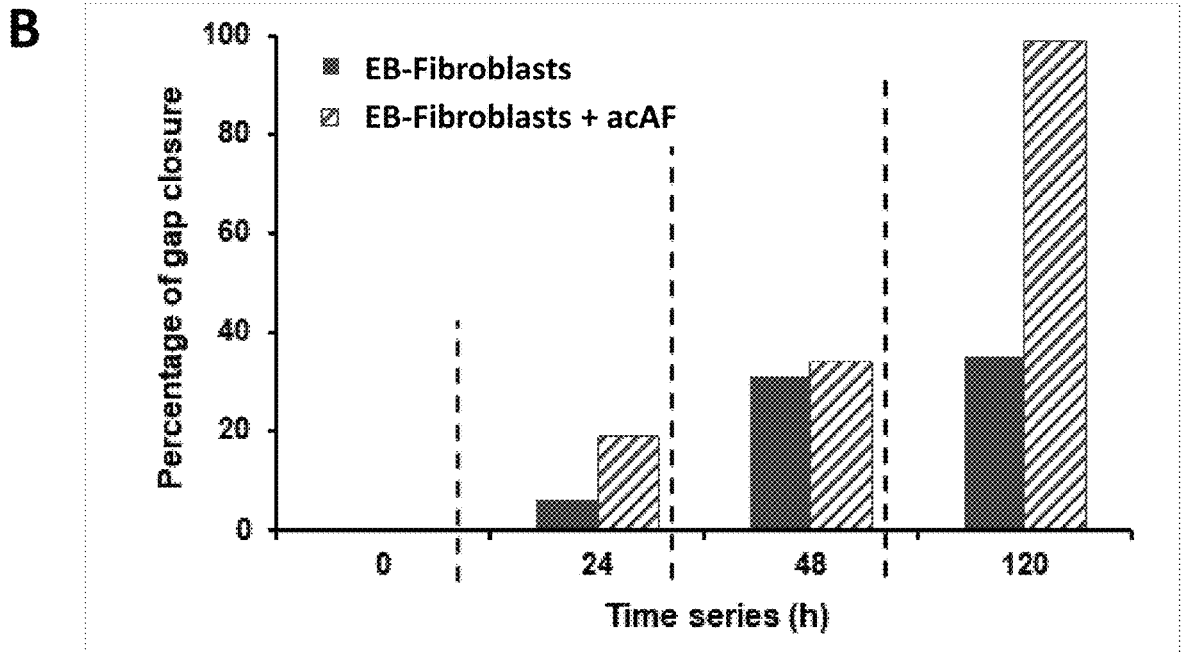
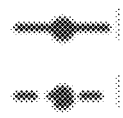
FIGs. 2A & 2B

METHODS OF TREATING EPIDERMOLYSIS BULLOSA WITH CELL-FREE AMNIOTIC FLUID COMPOSITIONS

CROSS-REFERENCE TO RELATED APPLICATIONS

This application claims the benefit of priority to U.S. Provisional Application No. 63/254,918, filed on Oct. 12, 2021, and U.S. Provisional Application No. 63/274,214, filed on Nov. 1, 2021. Each of the foregoing applications is incorporated herein by reference in its entirety.

FIELD OF THE INVENTION

The present disclosure relates to methods of treating epidermolysis bullosa (EB).

BACKGROUND OF THE INVENTION

Epidermolysis Bullosa (EB) is a group of rare genetic conditions that result in complications that can affect various parts of the body, including blistering of the skin and mucous membranes. EB is caused by mutations in genes involved in the attachment between or within the layers of epithelium, mucosa and skin. For example, dystrophic EB (DEB), including recessive dystrophic EB (RDEB) is caused by mutations in the COL7A1 gene, which encodes the collagen VII protein. Junction EB (JEB) is caused by mutations in the genes that encode the laminin 332 protein, i.e., the *LAMA*3, LAMB3 and/or LAMC2 genes. Several other genes are involved in different types of EB. The progressive nature of EB leads to scarring and contractures, causing reduced mobility, fusing of the fingers and toes causing mitten deformities, microstomia, significant disability, and skin cancer.

Currently no treatment exists for EB. Accordingly, there is a need for effective treatment of EB. Most investigational approaches focus on gene therapy to replace the defective mutations and other approaches include protein replacement therapy using recombinant proteins.

SUMMARY OF THE INVENTION

The present disclosure provides methods of treating a subject having epidermolysis bullosa (EB), comprising administering to the subject a therapeutically effective amount of a pharmaceutical composition comprising amniotic fluid substantially free of endogenous cells, thereby treating EB.

In some embodiments, the composition is substantially free of *lanugo* and *vernix*. In some embodiments, the composition is sterile or has been sterilized. In some embodiments, the composition further comprises pieces of (e.g., micronized, homogenized, morselized, lyophilized) amniotic membrane and/or Wharton's jelly. In some embodiments, the method comprises reconstituting the whole or part of the pharmaceutical composition from a lyophilized composition, e.g., amniotic fluid, amniotic membrane, or Wharton's jelly.

In some embodiments, the composition comprises a therapeutically effective amount of protein. In some embodiments, the protein is one or more of collagen VII, keratin, laminin, and decorin. In some embodiments, the composition comprises a therapeutically effective amount of cell-free mRNA. In some embodiments, the cell-free mRNA is a transcript or a fragment thereof of one or more genes selected from the group consisting of COL7A1, COL17A, COL17A1, KRT5, KRT14, KLHL24, PLEC, DST, EXPH5, CD151, LAMA3, LAMB3, LAMC2, ITGA3, ITGA6, ITGB4, FERMT1, and DCN. In some embodiments, the composition comprises a therapeutically effective amount of one or more neurotrophins. In some embodiments, the one or more neurotrophins are selected from the group consisting of nerve growth factor, brain-derived neurotrophic factor, and neurotrophin-3.

In some embodiments, the composition further comprises a protein composition exogenous to the amniotic fluid. In some embodiments, the protein composition comprises one or more of collagen VII, keratin, laminin, and decorin. In some embodiments, the composition further comprises a cell-free mRNA composition exogenous to the amniotic fluid. In some embodiments, the cell-free mRNA composition comprises a transcript or a fragment thereof of one or more genes selected from the group consisting of COL7A1, COL17A, COL17A1, KRT5, KRT14, KLHL24, PLEC, DST, EXPH5, CD151, LAMA3, LAMB3, LAMC2, ITGA3, ITGA6, ITGB4, FERMT1, and DCN.

In some embodiments, the composition further comprises, or is co-administered with, a penetration enhancer. In some embodiments, the composition is allogeneic relative to the subject. In some embodiments, the subject is human. In some embodiments, the composition is administered to the subject topically, subcutaneously, intradermally, intravenously, intracorneally, or intralocularly. In some embodiments, the composition is formulated as eye drops. In some embodiments, the composition is formulated as skin gel.

In some embodiments, the compositions of the present disclosure, including but not limited to decorin, modulate the transforming growth factor (TGF) signaling pathway. In some embodiments, the composition of the present disclosure facilitates wound healing. In some embodiments, the compositions of the present disclosure prevent, alleviate, or treat one or more signs, symptoms, or conditions associated with EB. In some embodiments, the one or more signs, symptoms, or conditions are selected from the group consisting of pain, pruritus, blisters, keratoderma, granulation, erosion, ulceration, pseudosyndactyly, open wounds, tissue scarring, tissue fibrosis, corneal opacification, corneal scarring, corneal ulcerations, cortical abrasions, blepharitis, ectropion, symblepharon, pterygium, caries, dilated cardiomyopathy, hypoalbuminemia, failure to thrive, muscular dystrophy, osteopenia, osteoporosis, and post-streptococcal glomerulonephritis.

BRIEF SUMMARY OF THE DRAWINGS

FIG. 2A depicts the gap area distance (fold over time 0) following treatment with the acellular amniotic fluid composition (or no treatment) starting at time 0. FIG. 2B depicts percentage of gap closure following treatment with the acellular amniotic fluid composition (or no treatment) starting at time 0.

DETAILED DESCRIPTION OF THE INVENTION

Figure 1:
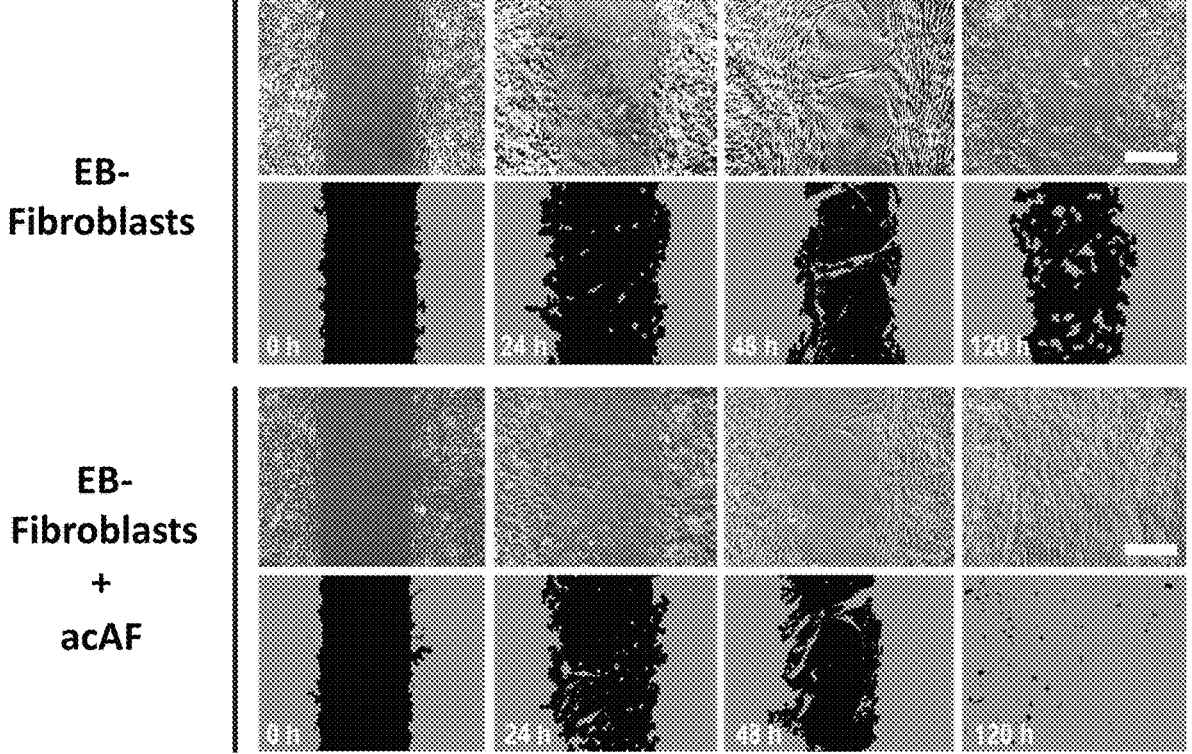
FIG. 1 depicts migration of primary fibroblasts harvested from RDEB patients ("EB-Fibroblasts") treated with the acellular amniotic fluid composition ("acAF") and untreated control at 0, 24, 48, and 120 hours after initiation of treatment.

The present disclosure now wilt be described more fully hereinafter. The disclosure may be embodied in many different forms and should not be construed as limited to the aspects set forth herein; rather, these aspects are provided so that this disclosure will satisfy applicable legal requirements.

1. Definitions

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

As used herein, a "subject" is an animal, such as a mammal, including a primate (such as a human, a non-human primate, e.g., a monkey) and a non-primate (such as a cow, a dog, a horse, a sheep, a rabbit, a cat, a rat, or a mouse). In some aspects of the invention, the subject is a human, such as a human having, or at risk of developing, EB. In some aspects, the subject is a pediatric subject, such as a neonate, an infant, or a child. In other aspects, the subject is an adult subject.

As used herein, "prevention" or "preventing," when used in reference to a disease (e.g., EB), refers to a reduction in likelihood of developing a disease or associated signs, symptoms, conditions, or complications, or a reduction in severity of a disease or associated signs, symptoms, conditions, or complications relative to a population having the same risk factors and not receiving treatment as described herein. The failure to develop a disease, or a delay in the time to develop associated signs, symptoms, conditions, or complications by days, weeks, months, or years is considered effective prevention. Prevention may require administration of more than one dose of the pharmaceutical compositions comprising acellular AF as described elsewhere herein.

As used herein, the term "treating" or "lent" in the context of treating a disease refers to a beneficial or desired result, such as reducing at least one associated sign, symptom, condition, or complication, e.g., pain or pruritus associated with skin conditions, e.g., blisters, in a subject. "Treatment" also refers to a prophylactic treatment, such as prevention of a disease or prevention of at least one sign, symptom, condition, or complication associated with the disease. "Treatment" can also mean prolonging survival as compared to expected survival in the absence of treatment.

II. Composition Comprising Acellular Amniotic Fluid

Provided herein are compositions comprising acellular amniotic fluid ("acAF") for use in treating a subject having EB according to the methods of the present disclosure.

A. Preparation of Acellular Amniotic Fluid Compositions

Amniotic fluid ("AF") surrounds a fetus during pregnancy and provides the fetus with a milieu of nutrients and compositions for optimal growth and development. Amniotic membrane, also called amnion, is the inner layer of the placenta and comprises a basement membrane and an avascular stromal matrix. Wharton's jelly is a mucoid connective tissue of the umbilical cord. Human amniotic fluid, amniotic membrane, Wharton's jelly, and associated tissues and compositions can be obtained from tissues and/or body fluids delivered by/from human donors upon informed consent, after delivery of a fetus, placenta, and said tissues and/or body fluids. In specific embodiments, amniotic fluid, amniotic membrane, Wharton's jelly, and/or associated tissues and compositions are donated by healthy human mothers daring routine cesarean deli-very. Accordingly, obtaining human amniotic fluid, amniotic membrane, Wharton's jelly, and associated tissues and compositions for use in the methods of present disclosure can be carried out without harm (including death) to donors (mother), infants, or newborns, and does not require induced termination of pregnancy. Each donor is tested using FDA approved methods and is found to be non-reactive for Hepatitis B, Hepatitis C, Human Immunodeficiency Virus type 1 & 2, Human T-Lymphotropic Virus type 1 & 2, Syphilis, West Nile Virus and Zika. Non-human amniotic fluid, amniotic membrane, Wharton's jelly, and associated materials can be obtained from non-human animal subjects according to the methods known in the art.

"Acellular amniotic fluid" (acAF) or "cell-free amniotic fluid", as used herein, refers to amniotic fluid that is substantially free of endogenous cells. "Substantially free of cells" as used herein refers to the status in which the cells are essentially absent, such as containing less than 1-10 cells/ml, or no cells. In specific embodiments, the acAF or the acAF composition provided herein comprise no cells. Without wishing to be bound by theory, crude human amniotic fluid can have about $5 \times 10^4$ cells/ml. The number of endogenous cells in an acAF or an acAF composition provided herein can be less than 0.1% or 0% of that in a crude amniotic fluid obtained from a donor. "Endogenous cells" as used herein refers to cells that were endogenously present in the crude amniotic fluid as obtained from the donor. Acellular amniotic fluid can be obtained by removing endogenous cells from amniotic fluid, and can be produced by any means known to those skilled in the art, such as applying centrifugation alone, filtration alone, serial filtration alone, combination of centrifugation and any type of filtration, or combination of centrifugation and serial filtration, to amniotic fluid samples obtained from subjects. In any step of preparation of acellular amniotic fluid, irradiation such as UV light or gamma rays can be included. Acellular amniotic fluid can be sterilized by standard methods, such as filtration, e.g., sterile filtration, irradiation, or combination thereof. In specific embodiments, an acAF is prepared by (1) irradiating with gamma ray crude amniotic fluid obtained from a healthy donor daring cesarean delivery upon informed consent; (ii) centrifuging the irradiated amniotic fluid at 1400×g for 15 minutes at 4° C.; (iii) collecting the supernatant and adjusting its pH to 7.4; and (iv) serially filtering the supernatant with a 40 micron and then a 0.2 micron filter. The acAF prepared by this procedure following steps (i)-(iv) above comprise no cells.

In some embodiments, the acellular amniotic fluid is substantially free of *lanugo, vernix* (also called *vernix* caseosa), and/or debris, in addition to being substantially cell-free. For example, the acAF provided herein can comprise *lanugo, vernix,* and/or debris that are less than 2%, less than 1%, less than 0.5%, less than 0.1%, or 0% relative to a crude amniotic fluid obtained from a donor. In specific embodiments, the acAF provided herein comprises no *lanugo, vernix,* and/or debris.

In some embodiments, the pH of the acellular amniotic fluid composition is adjusted to a therapeutically desired level or range of 6.5 to 8.5.

The acellular amniotic fluid or the composition comprising the acellular amniotic fluid can be lyophilized. The lyophilized composition can be reconstituted into a solution by adding a solvent used in the art, e.g., physiological saline. The compositions can be diluted or concentrated. In some embodiments, the composition is sterile or has been sterilized. The composition can be sterilized by subjecting the whole or part of the composition to any sterilization means known in the art, such as filtration, e.g., sterile filtration, irradiation, or combination thereof.

B. Protein and/or mRNA Compositions

In some embodiments, acellular amniotic fluid compositions of the present disclosure comprise a therapeutically effective amount of protein and/or mRNA. In some embodiments, the composition comprises a therapeutically effective amount of protein, A "therapeutically effective amount" or "effective amount" as used herein refers to the amount of a composition (e.g., protein, mRNA) effective to produce the intended pharmacological, therapeutic or preventive result, e.g., for treating EB.

In some embodiments, the protein in the composition is one or more of collagen VII, keratin, and laminin. In some embodiments, the composition comprises a therapeutically effective amount of mRNA, e.g., cell-free mRNA. "Cell-free mRNA" as used herein refers to extracellular mRNAs existing outside cells. In some embodiments, the mRNA is a transcript or a fragment thereof of one or more genes selected from the group consisting of COL7A1, COL17A, COL17A1, KRT5, KRT14, KLHL24, PLEC, DST, EXPH5, CD151A3, LAMB3, LAMC2, ITGA3, ITGA6, ITGB4, and FERMT1. In some embodiments, the acellular amniotic fluid compositions comprise one or more of collagen VII protein, collagen VII mRNA, keratin protein, keratin mRNA, laminin protein, and laminin mRNA. EB can be caused by mutations in one or more genes including but not limited to: COL7A1, COL17A, COL17A1, KRT5, KRT14, KLHL24, PLEC, DST, EXPH5, CD151, LAMA3, LAMB3, LAMC2, ITGA3, ITGA6, ITGB4, and FERMT1. Accordingly, the acellular amniotic fluid compositions of the present disclosure comprising the one or more proteins or mRNAs discussed above can provide therapeutic compositions that supplement one or more missing, dysfunctional, or non-functional proteins in EB subjects.

In some embodiments, the acellular amniotic fluid compositions comprise a modulator of the TGF signaling pathway, including but not limited to decorin. The compositions can comprise decorin protein and/or a transcript (e.g., mRNA, cell-free mRNA) or a fragment thereof of DCN. Decorin is a protein that belongs to the small leucine-rich proteoglycan family, and can modulate the TGF signaling pathway and/or interact with fibrinonectin, epidermal growth factor (EGF) receptor, and TGF-β, among other things. "Modulating the TGF signaling pathway", as used herein, refers to modulating (e.g., increasing or decreasing) the expression or function of molecules that are involved in the TGF signaling, such as TGF-α, TGF-β, EGF receptor, TGF-β receptor, downstream effectors and other TGF-related proteins.

In some embodiments, the composition comprises a therapeutically effective amount of one or more neurotrophins. In some embodiments, the one or more neurotrophins are selected from the group consisting of nerve growth factor, brain-derived neurotrophic factor, and neurotrophin-3.

C. Compositions Exogenous to Amniotic Fluid

In some embodiments, the compositions of the present disclosure include exogenous moieties or agents that were not natively present in the amniotic fluid. For example, in some embodiments, the composition further comprises amniotic membrane and/or Wharton's jelly. Amniotic membrane and/or Wharton's jelly can be micronized, homogenized, morselized, or lyophilized prior to being added to the acellular amniotic fluid composition. In some embodiments, the acellular amniotic fluid composition can be lyophilized prior to incorporation of the amniotic membrane and/or Wharton's jelly composition.

Including amniotic membrane or Wharton's jelly to the acellular amniotic fluid compositions of the present disclosure can increase concentrations of therapeutic proteins or mRNA in the composition, e.g., collagen VI, keratin, or laminin.

The compositions exogenous to the amniotic fluid may be a molecule that does not exist in the amniotic fluid. Alternatively, compositions exogenous to the amniotic fluid may be a molecule that can be identified in the amniotic fluid (e.g., collagen VII protein), but is added to the acellular amniotic fluid composition.

Accordingly, in some embodiments, the composition further comprises a protein composition exogenously added to the acellular amniotic fluid composition. In some embodiments, a recombinant protein of interest or a purified protein of interest can be added to the composition.

In some embodiments, the protein composition comprises one or more of collagen VII, keratin, laminin, and decorin. In some embodiments, the composition comprises a cell-free mRNA composition exogenously added to the acellular amniotic fluid composition. In some embodiments, the cell-free mRNA composition comprises a transcript or a fragment thereof of one or more genes selected from the group consisting of COL7A1, COL17A, COL17A1, KRT5, KRT14, KLHL24, PLEC, DST, EXPH5, CD151, LAMA3, LAMB3, LAMC2, ITGA3, ITGA6, ITGB4, and FERMT1 and DCN.

In some embodiments, the composition comprises a neurotrophin composition exogenously added to the acellular amniotic fluid composition. In some embodiments, the neurotrophin composition comprises protein or mRNA of at least one neurotrophins. In some embodiments, the at least one neurotrophins is selected from the group consisting of: nerve growth factor, brain-derived neurotrophic factor, and neurotrophin-3.

In some embodiments, the concentration of therapeutic molecules, e.g., therapeutic proteins oar mRNA, in the composition can be increased or decreased, as needed, relative to the concentration in the amniotic fluid as obtained from donors or subjects. The protein or mRNA concentration can be increased by, for instance, adding the protein or mRNA of interest in the form of amniotic membrane, Wharton's jelly, a recombinant protein, a purified protein, or exogenously prepared nucleic acids. Additionally, or alternatively, the concentration of a protein or mRNA of interest can be decreased relative to the original concentration. The protein or mRNA concentration can be decreased by, for instance, adding an acceptable dilutant, thereby diluting the protein or the mRNA of interest in the composition.

For example, the concentration of collagen VII can be measured in the acellular amniotic fluid composition, and then an additional amount of amniotic membrane, Wharton's jelly, a recombinant collagen VII protein, and/or a purified collagen VII protein can be added to increase the concentration of collagen VII to a therapeutically desired level. For example, collagen VII concentration in the acellular amniotic fluid composition can be about 0.3 mg/mL, which can be increased to about 0.6 mg/mL, about 0.9 mg/mL, about 1.2 mg/mL, about 1.5 mg/mL, about 1.8 mg/mL, about 2.1 mg/mL, about 2.4 mg/mL, about 2.7 mg/mL, about 3 mg/mL, or more. Alternatively, collagen VII concentration can be decreased by adding a vehicle, e.g., physiological saline, to the composition. For example, collagen VII concentration in the acellular amniotic fluid composition can be about 300 ng/mL, which can be decreased to about 270 ng/mL, about 240 ng/mL, about 210 ng/mL, about 180 ng/mL, about 150 ng/mL, about 120 ng/mL, about 90 ng/mL, about 60 ng/mL, about 30 ng/mL, or less. Similar processes can be applied to increase or decrease the concentration of other therapeutic molecules in the acellular amniotic fluid composition, such as laminin 332 and keratin.

In some embodiments, the pH of the composition comprising acellular amniotic fluid and an exogenous composition can be adjusted to a therapeutically desired level or range, e.g., 6.5 to 8.5. In some embodiments, the composition comprising acellular amniotic fluid and an exogenous composition can be lyophilized. The lyophilized composition can be reconstituted into a solution by adding a solvent used in the art, e.g., physiological saline.

D. Penetration Enhancers

In some embodiments, the composition further comprises, or is co-administered with, a penetration enhancer. A "penetration enhancer", as used herein, is a reagent that promotes the penetration of drugs through the epithelial barrier, e.g., a corneal barrier, and change the integrity of the epithelial cell layer. In some embodiments, a penetration enhancer is formulated for ocular delivery. In some embodiments, penetration enhancers that can be included in the composition or co-administered with the composition are include cyclodextrin, dimethylsulphoxide (DMSO), ethylenediaminetetraacetic acid (EDTA), sodium glycocholate and related cholate, Tween 20 (a non-ionic polysorbate surfactant), Brij 35 (polyoxyethylene lauryl ether), saponin, or bile salt. Without wishing to be bound by theory, penetration enhancers such as EDTA and cholates can transiently loosen the tight junctions between adjacent cells of the epithelium, e.g., corneal epithelium. Thus, penetration enhancers, when applied topically, e.g., to the eye, can enhance the delivery of therapeutic molecules, e.g., a protein, a peptide, or mRNA, through the epithelium.

In some embodiments, a penetration enhancer to be included in the composition or to be co-administered with the composition can be a chemical penetration enhancer. A "chemical penetration enhancer", as used herein, is a reagent that enhances transdermal drug delivery by perturbing the stratum corneum and/or other components of the skin. Chemical penetration enhancers that can be included in the composition or co-administered with the composition via transdermal drug delivery include pyrrolidones, alcohols, esters, water, esters sulfoxides (such as dimethyl sulfoxide) and their derivatives, hydrocarbons, terpenes and derivatives, rezone, and its analogs, amides (including urea and its derivatives), fatty acids, surfactants (nonionic, cationic, and anionic), oleodendrimers, ionic liquids, and deep eutectic solvents.

III. Dosage, Route, and Timing of Administration

A subject (e.g., a hire an subject having or at risk of developing EB) can be administered therapeutic amount of pharmaceutical compositions comprising acellular amniotic fluid.

In some embodiments, the composition is administered to the subject topically, subcutaneously, intradermally, intravenously, intracorneally, or intralocularly.

In some embodiments, the administration is repeated, for example, hourly, twice per day, daily, twice per week, weekly, biweekly, or monthly. In some embodiments, the administration is for a prescribed time period, e.g., for one month, two months, three months, four months, five months, six months, one year, longer, or indefinitely. After an initial treatment, the subsequent treatments can be administered less frequently relative to the initial treatment.

In some embodiments, the composition is administered in one dose, or in two or more doses. In some embodiments, the number, frequency, or amount of subsequent doses is dependent on the achievement of a desired therapeutic effect. In some embodiments, the composition is administered to a subject at the frequency and amount required to achieve a therapeutic effect. In some embodiments, the subject can be monitored for desired therapeutic effects and unwanted side effects associated with administration of the composition.

In some embodiments, the composition is formulated for delivery to a target organ, e.g., to the eye or to the skin. In some embodiments, the composition is formulated as eye drops for topical administration. In some embodiments, the composition is formulated as skin gel, ointment, or cream.

IV. Treating Subjects Having Epidermolysis Bullosa

Provided herein are methods of treating a subject having EB, or at risk of developing EB, comprising administering to the subject a therapeutically effective amount of a pharmaceutical composition comprising amniotic fluid substantially free of endogenous cells, thereby treating EB. A "therapeutically effective amount" or "effective amount" as used herein refers to the amount of a composition (e.g., acAF composition) effective to produce the intended pharmacological, therapeutic or preventive result. For example, in the method of treating a subject having EB provided herein, an effective amount includes an amount effective to reduce one or more signs, symptoms, or conditions associated with EB, e.g., an amount effective to: down-regulate TGF signaling pathway; increase cell proliferation, migration, or adhesion; increase wound healing; reduce or prevent one or more ocular manifestations of EB (e.g., pain, pruritus, corneal ° pacification, corneal scarring, corneal ulcerations, corneal abrasions, blepharitis, ectropion, symblepharon, pterygium, and loss of vision); reduce or prevent one or more skin manifestations of EB (e.g., pain, pruritus, blisters, keratoderma, granulation, erosion, ulceration, pseudosyndactyly, open wounds, tissue scarring, and tissue fibrosis; reduce or prevent one or more neural manifestations of EB (e.g., neuropathic pain, pruritus, and muscle weakness); and/or reduce or prevent one or more incidents, signs, or symptoms of caries, dilated cardiomyopathy, hypoalbuminemia, failure to thrive, muscular dystrophy, osteopenia, osteoporosis, and post-streptococcal glomerulonephritis. For example, if a given clinical treatment is considered effective when there is at least a certain percentage of reduction in a measurable parameter associated with EB, a therapeutically effective amount of a composition (e.g., acAF composition) for the treatment of EB is the amount necessary to obtain at least the certain percentage of reduction in that parameter. One skilled in the art can select the specific percentage, or range of percentages, of reduction of a measurable parameter by which to consider a treatment as effective according to the clinical and scientific context.

In some embodiments, the composition is allogeneic relative to the subject. In some embodiments, the subject is human. For example, the methods of present disclosure comprise treating a human subject having ER, or at risk of developing EB, comprising administering to the subject a therapeutically effective amount of a pharmaceutical composition comprising human amniotic fluid substantially free of endogenous cells.

In some embodiments, the compositions of c present disclosure supplement or replace one or more protein defective or absent in cells, tissues, or organs of subjects with EB. In some embodiments, the protein or proteins supplemented or replaced are one or more of collagen VII, keratin, laminin, decorin, or neurotrophin. In some embodiments, the compositions of the present disclosure supplement or replace mRNA defective or absent in cells, tissues, or organs of subjects with EB. In some embodiments, mRNA supplemented or replaced is mRNA of one or more of COL7A1, COL17A, COL17A1, KRT5, KRT14, KLHL24, PLEC, DST, EXPH5, CD151, LAMA3, LAMB3, LAMC2, ITGA3, ITGA6, ITGB4, and FERMT1, DCN, or variants thereof. In some embodiments, the compositions comprise therapeutic cell-free mRNA, and it is taken up by cells of subjects with EB for de nova production of proteins defective or missing in EB, i.e., causing cells to produce a replacement protein for the protein that has been defective or missing.

In some embodiments, the acellular amniotic fluid compositions modulate the TGF signaling pathway in a subject, which can result in increase or decrease in levels of TGE-$\alpha$, TGF-$\beta$, and/or other TGF-related proteins in cells, tissues, body fluids, or organs of the subject. The TGF-$\beta$ pathway is activated (e.g., upregulated) in some EB patients. Without wishing to be bound by theory, activation of the TGE-$\beta$ pathway is an independent modulator (exacerbator) of the clinical severity of EB, for example independent from the collagen 7 amount in the patient (Chacón-Solano et al. 2022 *Matrix Biol.* 111:189-206; Nyström et al. 2015 *EMBO Mol. Med.* 7(9):1211-1228; Odorisio et al. 2014 *Human Mol. Genet* 23:15; 3907-3922). In some embodiments, administration of the acellular amniotic fluid composition provided herein down-regulates (e.g., attenuates, decreases) the TGF signaling pathway by 5-100%, 10-100%, 20-100%, 30-100%, 40-100%, 50-100%, 60-100%, 70-100%, 80-100%, 20-90%, 30-90%, 40-90%, 50-90%, 60-90%, or 70-90% (e.g., by about 10-20%, 20-30%, 30-40%, 40-50%, 50-60%, 60-70%, 70-80%, 80-90%, or 90-100%), e.g., by about 10%, 15%, 20%, 25%, 30%, 35%, 40%, 45%, 50%, 55%, 60%, 65%, 70%, 75%, 80%, 85%, 90%, 95%, or 100%, or at least 5%, 10%, 15%, 20%. 25%, 30%, 35%, 40%, 45%, 50%, 55%, 60%, 65%, 70%, 75%, 80%, 85%, 90%, 95%, or 100%, as compared to a control without administration of the acellular amniotic fluid composition, Effects of acellular amniotic fluid on the TGF signaling pathway can be assessed by the standard methods such as those described in Odorisio et al. 2014 *Human Mol.* Genet. 23:15; 3907-3922. For example, human corneal fibroblasts can be cultured in standard cell culture media supplemented with 10% FBS (fetal bovine serum) until confluency. Then, the media is replaced with test media comprising the acellular amniotic fluid composition at varying dilutions in PBS (incrementally from 1% composition with 99% PBS to 99% composition % PBS), and the cells are incubated at 37° C. for 0, 3, 6, 12, 24 and 48 hours. After the incubation period, TCF-$\alpha$, TGF-$\beta$, ACTA2/$\alpha$-SMA, SERPINE1/PAI-1, BMP2K, decorin, TGF-$\beta$ R2, ZEB1, IL7, MMP3, DKK2, tenascin-C, and/or other TGF related proteins in the total cell lysates can be measured or in the supernatant by standard methods, such as ELISA or western blot. The amount of phosphorylated Smad3, phosphorylated Smad2, phosphorylated p38, phosphorylated ERK$\frac{1}{2}$, phosphorylated AKT, and their ratios over the unphosphorylated counterpart can be measured in total cell lysates by immunoblotting, quantified by densitometry and normalized to GAPDH, as the indicator of the TGF-$\beta$ pathway activity. Additionally, the expression of TGF-$\alpha$, TGF-$\beta$, ACTA2/$\alpha$-SMA, SERPINE1/PAI-1, BMP2K, decorin, TGF-$\beta$ R2, ZEB1, IL7, MMP3, DKK2, tenascin-C, and/or other TGE related mRNA molecules can be quantified by standard methods, such as mRNA isolation, cDNA synthesis, and subsequent real-time PCR quantification. TGF-$\beta$ receptor I inhibitor SB431542 can be included in the assay as a control.

In some embodiments, the compositions of the present disclosure are used to provide prophylactic, palliative or therapeutic relief to signs or symptoms of EB according to the methods of the present disclosure. In some embodiments, the methods of the present disclosure prevent, alleviate, or treat one or more signs, symptoms, or conditions associated with Eli. In some embodiments, the compositions and methods of the present disclosure prevent, alleviate, or treat one or more ocular manifestations of EB, such as corneal opacification, corneal scarring, corneal ulcerations, corneal abrasions, blepharitis, ectropion, symblepharon, pterygium, and loss of vision. Additionally or alternatively, the compositions and methods of the present disclosure can prevent, alleviate, or treat one or more skin manifestations of EB, such as blisters, keratoderma, granulation, erosion, ulceration, pseudosyndactyly, open wounds, tissue scarring, and tissue fibrosis, Additionally or alternatively, the compositions and methods of the present disclosure can prevent, alleviate, or treat one or more neural manifestations of EB, such as neuropathic pain, pruritus, and muscle weakness.

In specific embodiments, the compositions and methods of the present disclosure facilitates wound healing in EB subjects, such as wound healing in the skin, the cornea, or mucosal surface. Wound healing, replacement of damaged or destroyed tissue by newly produced tissue or cells, is a biological process in living organisms, such as humans, and is achieved through the steps of hemostasis, inflammation, proliferation, and remodeling (Sorg et al., 2017 *Eur. Surg. Res.* 58, 81-94). Chronic wounds, often characterized as wounds that remain open for three months or more, cost an estimated $10-20 billion dollars per year for the US healthcare system alone (Sen et al., 2009 *Wound Repair Regen,* 17, 763-771). Non-healing wounds cause significant morbidity and mortality, the burden of which has been compared to cancer (Armstrong et al., 2007 *Int. Wound J.* 4, 286-287). Chronic wounds result from disruption to one of four orchestrated phases that normal, acute wound healing undergoes described above: hemostasis, inflammation, proliferation, and remodeling (Sorg et al., 2017 *Eur. Surg. Res.* 58, 81-94). Dysregulation of any of these steps leads to non-healing ulcers or excessive scarring. Delayed, dysregulated, or impaired would healing, chronic wounds, and/or non-healing wounds are associated with EB and subjects having EB.

The compositions and methods provided herein can facilitate (e.g., increase) wound healing by about 0-100%, 20-100%, 30-100%, 40-100%, 50-100%, 60-100%, 70-100%, 80-100%, 20-90%, 30-90%, 40-90%, 50-905% 60-90%, 70-90%, 100-1000%, 200-1000%, 300-1000%, 400-1000%, 500-1000%, 600-1000%, 700-1000%, 800-1000%, 200-900%, 300-900%, 400-900%, 500-900%, 600-900%, 700-900%, or more than 1000% (e.g., by about 10-20%, 20-30%, 30-40%, 40-50%, 50-60%, 60-70%, 70-80%, 80-90%, 90-100%, 100-200%, 200-300%, 300-400%, 400-500%, 500-600%, 600-700%, 700-800%, 800-900%, 900-1000%, or more than 1000%), e.g., increased by about 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900%, 1000%, or more, or at least 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900%, 1000%, or more relative to healing of a control wound to which the acellular amniotic fluid composition of the present disclosure is not administered. Would healing can be measured by any standard methods for assessing wound healing in vitro, ex vivo, or in vivo, including but not limited to a scratch assay, a cell proliferation assay, a cell migration assay, a cell detachment assay, a cell adhesion assay, a collagen lattice contraction assay, or functional evaluation of repaired tissue (e.g., tissue integrity). Exemplary evaluation methods that can be used are provided in the present disclosure.

In some embodiments, the one or more signs, symptoms, or conditions are selected from the group consisting of pain, pruritus, blisters, keratoderma, granulation, erosion, ulceration, pseudosyndactyly, open wounds, tissue scarring, tissue fibrosis, corneal scarring, blepharitis, ectropion, symblepharon, pterygium, loss of vision, caries, dilated cardiomyopathy, hypoalbuminemia, failure to thrive, muscular dystrophy, osteopenia, osteoporosis, and post-streptococcal glomerulonephritis.

In some embodiments, the composition of the present disclosure, the acellular amniotic fluid composition, is administered in combination with a second therapy known to be effective in treating EB or preventing, alleviating, or treating one or more signs, symptoms, conditions, or complications associated with EB. The acellular amniotic fluid composition may be administered before, after, or concurrent with the second therapy.

The second therapy may be an additional therapeutic agent. The acellular amniotic fluid composition and the additional therapeutic agent can be administered in combination within the same composition, or co-administered as separate compositions. In some embodiments, the additional therapeutic agent is an anti-inflammatory agent, a pain medication, or an antibiotic. The acellular amniotic fluid composition can be administered in conjunction with a second therapy. Exemplary combination therapies include debridement, skin graft, and gene therapy.

EXAMPLES

The following examples are offered by way of illustration and not by way of limitation.

Example 1: Collagen VII and Decorin Concentrations in Acellular Amniotic Fluid Samples Acellular amniotic fluid was obtained from five human donors not having EB. The concentrations of collagen VII and decorin in the five acellular amniotic fluid samples were measured by commercially available ELISA kits according to the manufacturer's instructions.

As shown in Table 1, the collagen VII concentrations in acellular amniotic fluid samples ranged from approximately 77 ng/mL to approximately 987 ng/mL, with the average concentration of 335 ng/mL. Dystrophic epidermolysis bullosa (DEB) is caused by mutations in the gene encoding the collagen VII protein. The data demonstrates that acellular amniotic fluid compositions can be used to supplement therapeutic proteins, including collagen VII, in DEB patients. The concentrations of other proteins defective or missing in EB patients, e.g., laminin and keratin, in acellular amniotic fluid can also be measured.

Further, as shown in Table 1, the decorin concentrations in acellular amniotic fluid samples ranged from approximately 9 ng/mL to approximately 58 ng/mL, with the average concentration of 27 ng/mL, Decorin is known to modulate the TGF signaling pathway, among other things, and can play a therapeutic role in EB. The data demonstrates that acellular amniotic fluid compositions can be used to provide therapeutic proteins, including decorin, in EB patients.

TABLE 1

Collagen VII and Decorin Concentrations
in Acellular Amniotic Fluid Samples

| Acellular Amniotic Fluid Sample ID | Collagen VII Concentration (ng/mL) | Decorin Concentration (ng/mL) |
|---|---|---|
| 1 | 190.08 | 18.7 |
| 2 | 76.82 | 8.6 |
| 3 | 986.53 | 58.3 |
| 4 | 233.79 | 28.1 |
| 5 | 190.39 | 21.4 |

Example 2: mRNA Levels in Acellular Amniotic Fluid Samples

Levels of mutated or defective cell-free mRNA, responsible for pathogenesis of EB, COL7A1, LAMA3, LAMB3, LAMC2 were analyzed based on data derived from 98 samples of acellular amniotic fluid collected from subjects without EB.

As shown in Table 2, higher levels of COL7A1, LAMA3; LAMB3, and LAMC2 mRNA (detected using gene-specific probes), were present in acellular amniotic fluid samples, relative to control mRNA (detected using all gene-associated probes). Levels of cell-free mRNA of genes defective or missing in other types of EB, e.g., COL7A1, COL17A, COL17A1, KRT5, KRT14, KLHL24, PLEC, DST, EXPH5, CD151, ITGA3, ITGA6, ITGB4, and FERMT1 can also be analyzed.

The Table 2 data demonstrates that cell-free mRNA that are missing or defective in EB subjects are present at high concentrations in acellular amniotic fluid. Cell-free mRNA can be incorporated into cells of EB subjects leading to de novo production of proteins defective or missing in EB.

TABLE 2 mRNA Levels in Acellular Amniotic Fluid Samples

| Gene | Annotation | Note | Median ± S.D. (min-max) expression |
|---|---|---|---|
| All genes | — | median summarization of the expression of all gene-associated probes in the study | 3.61 ± 1.70 (1.84-13.86) |
| COL7A1 | collagen type VII, alpha 1 chain | COL7A1 | 8.07 ± 0.38 (6.99-8.88) |
| LAMA3 | laminin, alpha 3 subunit | part of laminin-332 (α3 chain) | 6.64 ± 0.45 (5.48-7.93) |
| LAMB3 | laminin, beta 3 subunit | part of laminin-332 (β3 chain) | 5.46 ± 0.28 (4.82-6.23) |
| LAMC2 | laminin, gamma 2 subunit | part of laminin-332 (γ2 chain) | 5.67 ± 0.35 (4.80-6.75) |

Example Acellular Amniotic Fluid Composition
Promotes Wound Healing

Experimental Methods

Amniotic fluid (crude amniotic fluid) was obtained from a healthy donor during cesarean delivery upon informed consent. Crude amniotic fluid was irradiated with gamma ray and then centrifuged at 1400×g for 15 minutes at 4° C. The supernatant was collected, pH was adjusted to 7.4, and then serially filtered with a 40 micron filter and a 0.2 micron filter, resulting in sterile acAF.

To investigate the effect of the acellular amniotic fluid composition ("acAF composition") on cell migration, an in vitro scratch assay was conducted as previously described by Pitzurra 2020 *J. Peridont. Res.* 55:287-295). Briefly, fibroblasts derived from recessive dystrophic epidermolysis Bullosa (RDEB) patients ("EB-Fibroblasts") were seeded at an optimal density for confluency into special migration silicon inserts in serum free media with or without the acAF composition (25% acAF in the serum free media) and incubated overnight (each group in duplicate). To segment the area-of-interest, binary masks were created from the raw phase-contrast images with ImageJ software, and the gap/wound closure percentage was quantified as described in Youssefian et al., 2021 *J. Invest. Dermatol.* 141(7):1754-1764. The migration rate and gap closure percentage were measured at 24, 48, and 120 h after treatment.

Results

As shown in FIGS. 1, 2A, and 2B, the gap area remained clearly detectable at 120 h in the untreated, control cells. In contrast, closure occurred between 48-120 hours in the acAF composition treated fibroblasts. These data demonstrate the ability of the acAF composition to facilitate fibroblast migration and facilitate wound healing.

Example 4: Acellular Amniotic Fluid
Down-Regulates Transforming Growth Factor
(TGF) Signaling Pathway Experimental Methods Sterile acAF was prepared according to the procedure described in Example 3. Effects of an acAF composition on the TGF signaling pathway was assessed by the standard methods such as those described in Odorisio et al, 2014 *Human Mol.* Genet. 23:15; 3907-3922. Briefly, EB-Fibroblasts derived from RDEB patients described in Example 3, and control fibroblasts derived from healthy, subjects ("Control Fibroblasts") were incubated in serum free media at an optimal density for 24 hours with or without 25% acAF composition or recombinant decorin (positive control). Cells were harvested and lysed at 48 hours. To assess activation of the TGF-β signaling pathway, phosphorylation of Smad3 was quantitated by immunoblotting of total cell lysate. The intensity as well as the ratio of phosphorylated Smad3 and unphosphorylated Smad3 was assessed.

Results

Figure 3:
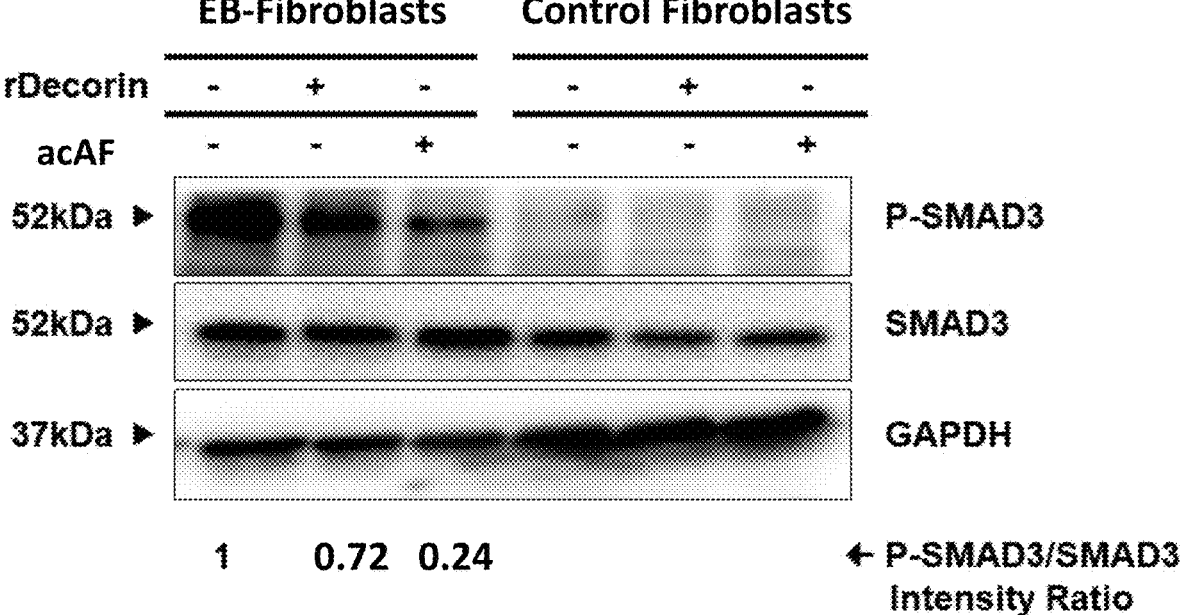
FIG. 3 depicts phosphorylated SMAD3 (P-SMAD3) immunoblotting of total lysate of fibroblasts derived from a recessive dystrophic epidermolysis bullosa ("RDEB") subject ("EB-Fibroblasts") and normal human breast fibroblasts ("Control Fibroblasts") treated with or without the acAF composition and/or recombinant decorin ("rDecorin").

Increased TGF-β signaling, as determined by increased phosphorylation of Smad3, a downstream target of TGF-β, was evident in the primary EB-Fibroblasts RDEB fibroblasts (FIG. 3, lane 1), Addition of recombinant decorin ("rDecorin"), an endogenous TGF-β inhibitor, resulted in a mild decrease in smad3 phosphorylation (FIG. 3, lane 2). Importantly, EB-Fibroblasts RDEB primary fibroblasts treatment with a 25% acAF composition for 24 hours showed a significant decrease of Smad3 phosphorylation (FIG. 3, lane 3). Non-detectable phosphorylated Smad3 was observed in Control Fibroblasts, either with or without treatment with the decorin and/or acAF compositions. These data demonstrate that the acAF composition of the present disclosure down-regulates the TGF signaling pathway. Down-regulation of the TGF pathway can treat EB and ameliorate signs and symptoms associated with EB in a subject independent of the collagen amount in the tissue of the subject.

Example 5: Functional in Vitro Assays

Proper cell proliferation, migration and attachment are key cellular functions for adequate tissue homeostasis. These cellular functions are typically altered in EB patients resulting in excessive blistering and inadequate wound healing. Cells derived from EB subjects, e.g., fibroblasts, keratinocytes or ocular epithelial cells, exhibit similar altered cellular functions in vitro.

Exemplary in vitro models of EB (e.g., EB cells or EB cell lines) are established as follows. Cells, such as fibroblasts, keratinocytes, and ocular epithelial cells, are harvested from human and non-human subjects having FE, or having a mutation that causes EB, and cultured in vitro. EB cells are also generated by knocking in or knocking down one or more genes or proteins associated with EB, e.g., COL7A1, LAMA3, LAMB3, LAMC2, COL17A, COL17A1, KRT5, KRT14, KLHL24, PLEC, DST, EXPH5, CD151, ITGA3, ITGA6, ITGB4, and FERMT1. From these EB cells, a primary cell culture is established, and optionally passaged. Immortalized EB cell lines are also established. The therapeutic effects of the compositions of the present disclosure are evaluated by cellular assays including the following:

1. Cell Proliferation Assay

EB cells and control cells are cultured with the compositions of the present disclosure comprising acellular amniotic fluid having varying concentrations or amounts of a therapeutic molecule, e.g., a protein or mRNA of the gene defective in EB. For example, the cells are cultured in serum free cell culture media comprising acellular amniotic fluid at varying dilutions, e.g., 100%, 75%, 50%, 25%, 10%, 1%, or 0.3% acellular amniotic fluid. Cell proliferation is measured by methods known to those skilled in the art, such as DNA synthesis cell proliferation assays, metabolic cell proliferation assays (e.g., MIT assay), detecting proliferation markers, among others.

2. Cell Migration Assay

EB cells are cultured with the compositions of the present disclosure comprising acellular amniotic fluid having varying concentrations or amounts of a therapeutic molecule, e.g., a protein or mRNA of the gene defective in EB. For example, the cells are cultured in serum free cell culture media comprising acellular amniotic fluid at varying dilutions, e.g., 100%, 75%, 50%, 25%, 10%, or 1% acellular amniotic fluid. Cell migration properties are studied by methods known in the art, such as a Boyden chamber, cell culture wounds, scratch assays among others.

3. Cell Detachment Assay

EB cells are cultured with the compositions of the present disclosure comprising acellular amniotic fluid having varying concentrations or amounts of a therapeutic molecule, e.g., a protein or mRNA of the gene defective in EB. For example, the cells are cultured in serum free cell culture media comprising acellular amniotic fluid at varying dilutions, e.g., 100%, 75%, 50%, 25%, 10%, or 1% acellular amniotic fluid. The cell detachment properties are measured by standard methods, such as those described in Löffek et al. 2014 *PLOS One* 9(2):e87263 and Jacków et al. 2016 *J. Invest. Dermatol.* 136:1346-1354.

For example, fibroblast or corneal epithelial cells are seeded in cell culture plates, and cultured for 24 hours. Subsequently, cells are washed with phosphate buffer saline (PBS) and treated with trypsin/EDTA (0.05/0.02%) for 10, 6, 4, 2, 1, and 0 minutes followed by another PBS wash. The adherent cells are stained with 0.5% crystal violet in distilled water for 30 minutes, lysed with 1% sodium dodecyl sulfate (SDS), and the percentage of adherent cells can be determined by the measure of the absorbance at 540, 590, or 595 nm using a spectrophotometer. Results are expressed as a percentage relative to 0 minute (trypsin untreated).

Additionally, or alternatively, a centrifugal-force assay is conducted. Briefly, cell culture plates are coated with the compositions of the present disclosure overnight and EB cells are seeded a period of time ranging from 10 minutes to hours. Subsequently, the cell culture plates are centrifuged at different forces and non-adherent cells are washed with PBS. Adherent cells are fixed, stained with crystal violet, lysed and absorbance of the dye is measured using a spectrophotometer.

4. Cell Adhesion Assay

EB cells are cultured with the compositions of the present disclosure comprising acellular amniotic fluid having varying concentrations or amounts of a therapeutic molecule, e.g., a protein or mRNA of the gene defective in EB. For example, the cells are cultured in serum free cell culture media comprising acellular amniotic fluid at varying dilutions, e.g., 100%, 75%, 50%, 25%, 10%, 1%, or 0% acellular amniotic fluid. The cell adhesion properties are measured by standard methods, including those described in Chen et al. 1999 *Experian. Cell Res.* 249(2):231-239. Briefly, cell culture plates are coated with the composition overnight. Fibroblast or corneal epithelial cells are added and allowed to attach for a period of time such as 1.5 hours at 37° C. Subsequently, unattached cells are removed by washing them with PBS. Adherent cells are stained for 15 min with 0.5% crystal violet and washed extensively with distilled water, solubilized in 1% SDS, and quantified by measuring the absorbance.

5. Collagen Lattice Contraction Assay

EB cells are cultured with the compositions of the present disclosure comprising acellular amniotic fluid having varying concentrations or amounts of a therapeutic molecule, e.g., a protein or mRNA of the gene defective in EB. For example, the cells are cultured in serum free cell culture media comprising acellular amniotic fluid at varying dilutions, e.g., 100%, 75%, 50%, 25%, 10%, or 1%, or 0% acellular amniotic fluid. The collagen lattice contraction properties are measured by standard methods, including those described in Odorisio et al. 2014 *Human Mol.* Genet. 23:15:3907-3922. In brief, collagen solution is produced by mixing acidic-soluble type I collagen (Symatese Biomateriaux, Chaponost, France) 3 mg/ml, a 5-fold concentration of DMEM and a buffer solution (0.05 M NaGH, 2.2% NaHCO3, 200 mM HEPES) in the ratio 7:2:1. Collagen solution is mixed with cell suspension in serum-free medium, plated in six-well cell culture cluster (Costar; Corning, N.Y., USA) and gelled at 37° C. for 30 min. The final concentration of collagen can be 2.1 mg/ml. Serum-free DMEM is poured onto the gel to prevent the surface from dehydrating. After 12 h of incubation, the gel is detached from each well and left floating. Surface area of gel samples is measured at detachment (time 0) and after 24 and 48 h. The contraction of the gel can be expressed as percentage of initial lattice area following the formula: A2/A1×100, where A1 is the initial gel area and A2 the area at the observed interval. Three culture plates is used for each experimental group. The assay is conducted on the following experimental groups: (1) gelification performed with 0.25 ng/ml of recombinant human TGF-β1 (R&D Systems) (contraction positive control); (2) gelification performed with 200 nM recombinant human DCN (R&D Systems) and/or in the absence of TGE-β1 (0.25 ng/ml) (negative control); and (3) gelification with a 0%, 50%, or 100% acAF composition (experimental group).

Example 6: Treatment of Epidermolysis Bullosa in Animal Models in Vivo

The compositions of the present disclosure comprising acellular amniotic fluid are administered to animal models of EB, and their therapeutic effects are tested. Several EB animal models are available in various species, including cows, dogs, horses, sheep, cats, rats, and mice. Exemplary EB animal models are described for instance in Bruckner-Tuderman et al. 2010 *J. Invest. Dermatol.* 130:1485-1488, which is herein incorporated by reference in its entirety. EB animal models include knock-out models, conditional knock-out models, and hypomorphic models.

Amniotic fluid and/or placental materials are donated by healthy mothers during routine cesarean delivery. The collection of the amniotic fluid or placental materials does not entail harm to mothers or newborns, and does not require induced termination of pregnancy. Each donor is tested using FDA approved methods and is found to be non-reactive for Hepatitis B, Hepatitis C, Human Immunodeficiency Virus type 1 & 2, Human T-Lymphotropic Virus type 1 & 2, Syphilis, West Nile Virus and Zika. acAF compositions are prepared as provided in the present disclosure.

The compositions are administered to EB and control subjects as eye drops. Additionally or alternatively, the compositions are delivered to EB and control subjects by topical, subcutaneous, intradermal, intravenous, intracorneal, or intraocular administration. Additionally or alternatively, the compositions are formulated as gels and ointments, and a permeability enhancer is added, and administered to EB and control subjects. In some embodiments, the compositions are combined with a pharmaceutical such as drugs to manage pain or inflammation and co-administered to EB and control subjects.

In one example, a hypomorphic mouse model that produces about 10% of wild-type collagen VII protein ("C7Hypo") described in Fritsch et al. 2008 *J. Clin, Invest.* 8; 118(5):1669-1679 is used as an EB animal model. In brief, a central corneal epithelial defect of up to 2-mm in diameter (trephine defined) without damaging the stroma in both eye (n=6 animals but this number can be flexible depending on animal availability) is created in the C7Hypo mice between 8-10 weeks of age. Immediately after, the epithelium defect is measured, photographed, and graded using fluorescein stain to define baseline. Ten (10) uL of the acAF composition is administered topically on the right eye and 10 uL of saline (control) is administered topically on the left. The topical product is let sit on the cornea for a period of time (e.g., 5 minutes). The topical administration is repeated 6 times a day until epithelium defect resolves. Corneal healing is compared between acAF composition treated corneas and the control, untreated corneas. At the end of the study, corneas are harvested for qPCR, Western Blot (WB), and immunofluorescence/immunohistochemistry stains to quantitate mRNA and protein expression of collagen 7, TGF-β, α-SMA, decorin, Ki67, MMP9, tenascin-C, and/or β-III tubulin.

All citations to references, including, for example, citations to patents, published patent applications, and articles, are herein incorporated by reference in their entirety.

The section headings used herein are for organizational purposes only and are not to be construed as limiting the subject matter described in any way.

What is claimed is:

1. A method of treating epidermolysis bullosa (EB) in a subject, said method comprising: administering to the subject a therapeutically effective amount of a pharmaceutical composition comprising amniotic fluid substantially free of endogenous cells, thereby treating epidermolysis bullosa.

2. The method of claim 1, wherein the composition is substantially free of *lanugo* and *vernix*.

3. The method of claim 1, wherein the composition is sterile or has been sterilized.

4. The method of claim 1, wherein the composition further comprises amniotic membrane or Wharton's jelly.

5. The method of claim 1, wherein the composition is reconstituted from lyophilized amniotic fluid.

6. The method of claim 1, wherein the composition comprises a therapeutic protein endogenous and/or exogenous to the amniotic fluid.

7. The method of claim 6, wherein the therapeutic protein is one or more of collagen VII, keratin, laminin, and decorin.

8. The method of claim 1, wherein the composition comprises a therapeutically effective amount of cell-free mRNA endogenous and/or exogenous to the amniotic fluid.

9. The method of claim 8, wherein the cell-free mRNA is a transcript or a fragment thereof of one or more genes selected from the group consisting of COL7A1, COL17A, COL17A1, KRT5, KRT14, KLHL24, PLEC, DST, EXPH5, CD151, LAMA3, LAMB3, LAMC2, ITGA3, ITGA6, ITGB4, FERMT1, and DCN.

10. The method of claim 1, wherein the composition comprises a therapeutically effective amount of protein or mRNA of one or more neurotrophins.

11. The method of claim 10, wherein the one or more neurotrophins are selected from the group consisting of nerve growth factor, brain-derived neurotrophic factor, and neurotrophin-3.

12. The method of claim 1, wherein the composition further comprises, or is co-administered with, a penetration enhancer.

13. The method of claim 1, wherein the composition is allogeneic relative to the subject.

14. The method of claim 1, wherein the composition is administered to the subject topically, subcutaneously, intradermally, intravenously, intracorneally, or intraocularly.

15. The method of claim 1, wherein the composition is formulated as eye drops or skin gel.

16. The method of claim 1, wherein the therapeutically effective amount of the composition modulates a transforming growth factor (TGF) signaling pathway.

17. The method of claim 1, wherein the therapeutically effective amount of the composition facilitates wound healing.

18. The method of claim 1, wherein the composition prevents, alleviates, or treats one or more signs, symptoms, or conditions associated with epidermolysis bullosa selected from the group consisting of pain, pruritus, blisters, keratoderma, granulation, erosion, ulceration, pseudosyndactyly, open wounds, tissue scarring, tissue fibrosis, corneal opacification, corneal ulceration, corneal abrasions, corneal scarring, blepharitis, ectropion, symblepharon, pterygium, loss of vision, caries, dilated cardiomyopathy, hypoalbuminemia, failure to thrive, muscular dystrophy, osteopenia, osteoporosis, and post-streptococcal glomerulonephritis.

19. The method of claim 1, wherein the pharmaceutical composition comprises no cells and is sterile.

20. The method of claim 1, wherein treating comprises treating one or more ocular manifestations of epidermolysis bullosa or one or more skin manifestations of epidermolysis bullosa.

* * * * *